US006887979B2

(12) United States Patent
Nakamori et al.

(10) Patent No.: US 6,887,979 B2
(45) Date of Patent: May 3, 2005

(54) METHOD OF PREVENTING DECREASE IN THE ACTIVITY OF PROTEIN DUE TO FREEZING AND USE OF POLYPEPTIDE IN THE PRODUCTION OF PROTEIN ACTIVITY DECREASE PREVENTING AGENT

(75) Inventors: Shigeru Nakamori, Fukui-Ken (JP); Hiroshi Takagi, Fukui (JP); Masakazu Takahashi, Fukui (JP); Kazuhisa Tsujimoto, Fukui (JP); Hideyuki Yamada, Fukui (JP)

(73) Assignee: Seiren Kabushiki Kaisha, Fukui (JP)

( * ) Notice: Subject to any disclaimer, the term of this patent is extended or adjusted under 35 U.S.C. 154(b) by 0 days.

(21) Appl. No.: 10/148,306

(22) PCT Filed: Oct. 1, 2001

(86) PCT No.: PCT/JP01/08653

§ 371 (c)(1),
(2), (4) Date: May 29, 2002

(87) PCT Pub. No.: WO02/26800

PCT Pub. Date: Apr. 4, 2002

(65) Prior Publication Data

US 2003/0166186 A1 Sep. 4, 2003

(30) Foreign Application Priority Data

Sep. 29, 2000 (JP) ........................................ 2000-300983

(51) Int. Cl.$^7$ ............................ C07K 1/00; C12P 21/06; C12N 9/00; C12N 1/20; C12N 15/00
(52) U.S. Cl. ............................... 530/350; 435/4; 435/6; 435/183 T; 435/252.3; 435/320.1; 435/325; 435/348; 435/85; 435/86
(58) Field of Search ............................ 435/4, 6, 85, 86, 435/183 T, 252.3, 320.1, 325, 348; 530/350

(56) References Cited

PUBLICATIONS

Tsujimoto, K., et al. "Cryoprotective Effect of the Serine–Rich Repetitive Sequence in Silk Protein Sericin" *Biochem.*, vol. 129, p. 979–986, (2001).

Honjoh, K., et al. "Cryoprotective Activities of Group 3 Late Embryogenesis Abundant Proteins from *Chlorella vulgaris* C–27" *Biosci. Biotechnol. Biochem.*, vol. 64, No. 8, p. 1656–1663, (2000).

Garel, A., et al. "Structure and Organization of the *Bombyx mori* Sericin 1 Gene and of the Sericins 1 Deduced . . . cDNA" *Insect. Biochem. Molec. Biol.*, vol. 27, No. 5, p. 469–477, (1997).

(Continued)

*Primary Examiner*—Manjunath Rao
(74) *Attorney, Agent, or Firm*—Ladas & Parry LLP

(57) ABSTRACT

An objective of the present invention is to provide a means to prevent freeze-induced decrease in protein activity. The present invention relates to a method for preventing freeze-induced decrease in protein activity comprising adding a polypeptide comprising the following amino acid sequence (I) to a protein to be frozen. Further, the present invention relates to use of a polypeptide comprising the following amino acid sequence (I) to produce an agent for preventing freeze-induced decrease in protein activity:

(SEQ ID NO: 1)
Ser-Ser-Thr-Gly-Ser-X1-Ser-X2-Thr-Asp-X3-X4-X5-X6-
X7-X8-Gly-Ser-X9-Thr-Ser-Gly-Gly-Ser-Ser-Thr-Tyr-
Gly-Tyr-Ser-Ser-X10-X11-X12-X13-Gly-X14-Val (I).

18 Claims, 3 Drawing Sheets

OTHER PUBLICATIONS

Dav., R.S., et al. "A Low Temperature Induced Apoplastic Protein Isolated from *Arachis Hypogaea*" *Phytochemistry*, vol. 49, No. 8, p. 2207–2213, (1998).

Meijer, P., et al. "Directed evolution of a type I antifreeze protein expressed in *Escherichia coli* with sodium chloride as selective . . . tolerance" *Protein Engineering*, vol. 9, No. 11, p. 1051–1054, (1996).

Wisniewski, M., et al. "Purification, immunolocalization, cryoprotective, and antifreeze activity of PCA60: . . . (*Prunus persica*)" *Physiologia Plantarum*, vol. 105, p. 600–608, (1999).

Kazuoka, T., et al. "Purification and Characterization of COR85–Oligomeric Complex from Cold–Acclimated Spinach" *Plant Cell Physiol.*, vol. 35, No. 4, p. 601–611, (1994).

Okamoto, H., et al. "Structural Analysis of Sericin Genes", *J. of Biological Chemistry* vol. 257, No. 24, p. 15192–15199, (1982).

Database Biosis 'Online!Biosciences Information Service. Troiskaya, N. "Comparison of procedures of storing cultures of bacillus–thuringiensis–var–galleriae" *Prikladnaya Biokhimiya i Mikrobiologiya* (1979) vol. 15, No. 3, pp. 402–408. XP–002288375.

Database WPI, Section Ch, Week 198621, "Composition for eryoconservation of bovins sperm –contains sucrose or lactose and supplementary seriein..." (1985) XP–002288358.

Database Biosis 'Online ! Biosciences Information Service. Krokhina, V., et al., "Use of sericin during cultivation and drying of soil bacteria" *Prikladnaya Biokhimiya i Mikrobiologiya* (1980) vol. 16, No. 2, pp. 254–256. XP–002288376.

(a) CBB STAINING, (b) DETECTION OF 6 × His TAG BY Ni-NTA
1. control(pQE vector), 2. SP 2 (serD), 3. SP 4 (serT), 4. SP 6 (serH), 5. SP 8 (serO)

F I G. I

SEQUENCE LISTING

```
<160> NUMBER OF SEQ ID NOS: 21

<210> SEQ ID NO 1
<211> LENGTH: 38
<212> TYPE: PRT
<213> ORGANISM: Artificial
<220> FEATURE:
<223> OTHER INFORMATION: CONSENSUS SEQUENCE
<220> FEATURE:
<221> NAME/KEY: MISC_FEATURE
<222> LOCATION: (6)..(6)
<223> OTHER INFORMATION: Xaa represents Ser or Thr
<220> FEATURE:
<221> NAME/KEY: MISC_FEATURE
<222> LOCATION: (8)..(8)
<223> OTHER INFORMATION: Xaa represents Asn or Thr
<220> FEATURE:
<221> NAME/KEY: MISC_FEATURE
<222> LOCATION: (11)..(11)
<223> OTHER INFORMATION: Xaa represents Ser or Ala
<220> FEATURE:
<221> NAME/KEY: MISC_FEATURE
<222> LOCATION: (12)..(12)
<223> OTHER INFORMATION: Xaa represents Asn or Ser
```

-continued

```
<220> FEATURE:
<221> NAME/KEY: MISC_FEATURE
<222> LOCATION: (13)..(13)
<223> OTHER INFORMATION: Xaa represents Ser or Thr
<220> FEATURE:
<221> NAME/KEY: MISC_FEATURE
<222> LOCATION: (14)..(14)
<223> OTHER INFORMATION: Xaa represents Asn, Asp, or Lys
<220> FEATURE:
<221> NAME/KEY: MISC_FEATURE
<222> LOCATION: (15)..(15)
<223> OTHER INFORMATION: Xaa represents Ser, Asn, or Lys
<220> FEATURE:
<221> NAME/KEY: MISC_FEATURE
<222> LOCATION: (16)..(16)
<223> OTHER INFORMATION: Xaa represents Ala, Thr, or Val
<220> FEATURE:
<221> NAME/KEY: MISC_FEATURE
<222> LOCATION: (19)..(19)
<223> OTHER INFORMATION: Xaa represents Ser, or Arg
<220> FEATURE:
<221> NAME/KEY: MISC_FEATURE
<222> LOCATION: (32)..(32)
<223> OTHER INFORMATION: Xaa represents Asn, Ser,  Asp, or Arg
<220> FEATURE:
<221> NAME/KEY: MISC_FEATURE
<222> LOCATION: (33)..(33)
<223> OTHER INFORMATION: Xaa represents Ser,  Asn, His, or Cys
<220> FEATURE:
<221> NAME/KEY: MISC_FEATURE
<222> LOCATION: (34)..(34)
<223> OTHER INFORMATION: Xaa represents Arg or Gly
<220> FEATURE:
<221> NAME/KEY: MISC_FEATURE
<222> LOCATION: (35)..(35)
<223> OTHER INFORMATION: Xaa represents Asp or Gly
<220> FEATURE:
<221> NAME/KEY: MISC_FEATURE
<222> LOCATION: (37)..(37)
<223> OTHER INFORMATION: Xaa represents Ser or Arg

<400> SEQUENCE: 1

Ser Ser Thr Gly Ser Xaa Ser Xaa Thr Asp Xaa Xaa Xaa Xaa Xaa Xaa
1               5                   10                  15

Gly Ser Xaa Thr Ser Gly Gly Ser Ser Thr Tyr Gly Tyr Ser Ser Xaa
            20                  25                  30

Xaa Xaa Xaa Gly Xaa Val
        35

<210> SEQ ID NO 2
<211> LENGTH: 38
<212> TYPE: PRT
<213> ORGANISM: Artificial
<220> FEATURE:
<223> OTHER INFORMATION: FRAGMENT FOR RESISTANCE AGAINST DEHYDRATION
      STRESS

<400> SEQUENCE: 2

Ser Ser Thr Gly Ser Ser Ser Asn Thr Asp Ser Asn Ser Asn Ser Ala
1               5                   10                  15

Gly Ser Ser Thr Ser Gly Gly Ser Ser Thr Tyr Gly Tyr Ser Ser Asn
            20                  25                  30

Ser Arg Asp Gly Ser Val
        35

<210> SEQ ID NO 3
<211> LENGTH: 76
<212> TYPE: PRT
<213> ORGANISM: Artificial
<220> FEATURE:
<223> OTHER INFORMATION: FRAGMENT FOR RESISTANCE AGAINST DEHYDRATION
```

STRESS

<400> SEQUENCE: 3

Ser Ser Thr Gly Ser Ser Asn Thr Asp Ser Asn Ser Asn Ser Ala
1               5                   10                  15

Gly Ser Ser Thr Ser Gly Gly Ser Ser Thr Tyr Gly Tyr Ser Ser Asn
                20                  25                  30

Ser Arg Asp Gly Ser Val Ser Ser Thr Gly Ser Ser Asn Thr Asp
            35                  40                  45

Ser Asn Ser Asn Ser Ala Gly Ser Ser Thr Gly Gly Ser Ser Thr
    50                  55                  60

Tyr Gly Tyr Ser Ser Asn Ser Arg Asp Gly Ser Val
65                  70                  75

<210> SEQ ID NO 4
<211> LENGTH: 61
<212> TYPE: DNA
<213> ORGANISM: Artificial
<220> FEATURE:
<223> OTHER INFORMATION: SYNTHETIC DNA

<400> SEQUENCE: 4
gtgatcaatc gaaggtcgct cgagtactgg ttcttcttct aacaccgact ctaactctaa    60
c                                                                   61

<210> SEQ ID NO 5
<211> LENGTH: 69
<212> TYPE: DNA
<213> ORGANISM: Artificial
<220> FEATURE:
<223> OTHER INFORMATION: SYNTHETIC DNA

<400> SEQUENCE: 5
tctgctggtt cttctacctc tggtggttct tctacctacg gttactcttc taactctcgt    60
gacggttct                                                           69

<210> SEQ ID NO 6
<211> LENGTH: 65
<212> TYPE: DNA
<213> ORGANISM: Artificial
<220> FEATURE:
<223> OTHER INFORMATION: SYNTHETIC DNA

<400> SEQUENCE: 6
gtttcttcta ccggttcttc ttctaacacc gactctaact ctaactctgc tggttcttct    60
acctc                                                               65

<210> SEQ ID NO 7
<211> LENGTH: 65
<212> TYPE: DNA
<213> ORGANISM: Artificial
<220> FEATURE:
<223> OTHER INFORMATION: SYNTHETIC DNA

<400> SEQUENCE: 7
tggtggttct tctacctacg gttactcttc taactctcgt gacggatccg tttaatagct    60
gagcg                                                               65

<210> SEQ ID NO 8
<211> LENGTH: 69
<212> TYPE: DNA

<213> ORGANISM: Artificial
<220> FEATURE:
<223> OTHER INFORMATION: SYNTHETIC DNA

<400> SEQUENCE: 8
cagagttaga gttagagtcg gtgttagaag aagaaccagt actcgagcga ccttcgattg    60
atcactgca                                                            69

<210> SEQ ID NO 9
<211> LENGTH: 69
<212> TYPE: DNA
<213> ORGANISM: Artificial
<220> FEATURE:
<223> OTHER INFORMATION: SYNTHETIC DNA

<400> SEQUENCE: 9
aaacagaacc gtcacgagag ttagaagagt aaccgtaggt agaagaacca ccagaggtag    60
aagaaccag                                                            69

<210> SEQ ID NO 10
<211> LENGTH: 65
<212> TYPE: DNA
<213> ORGANISM: Artificial
<220> FEATURE:
<223> OTHER INFORMATION: SYNTHETIC DNA

<400> SEQUENCE: 10
accagaggta gaagaaccag cagagttaga gttagagtcg gtgttagaag aagaaccggt    60
agaag                                                                65

<210> SEQ ID NO 11
<211> LENGTH: 65
<212> TYPE: DNA
<213> ORGANISM: Artificial
<220> FEATURE:
<223> OTHER INFORMATION: SYNTHETIC DNA

<400> SEQUENCE: 11
aattcgctca gctattaaac ggatccgtca cgagagttag aagagtaacc gtaggtagaa    60
gaacc                                                                65

<210> SEQ ID NO 12
<211> LENGTH: 20
<212> TYPE: DNA
<213> ORGANISM: Artificial
<220> FEATURE:
<223> OTHER INFORMATION: serD GENE FOR PCR PRIMER

<400> SEQUENCE: 12
aaggtcgctc gagtaccggt                                                20

<210> SEQ ID NO 13
<211> LENGTH: 20
<212> TYPE: DNA
<213> ORGANISM: Artificial
<220> FEATURE:
<223> OTHER INFORMATION: serD GENE FOR PCR PRIMER

<400> SEQUENCE: 13
cgctcagact cgagacagat                                                20

<210> SEQ ID NO 14
<211> LENGTH: 17

```
<212> TYPE: DNA
<213> ORGANISM: Artificial
<220> FEATURE:
<223> OTHER INFORMATION: serD GENE FOR PCR PRIMER

<400> SEQUENCE: 14
gttttcccag tcacgac                                                    17

<210> SEQ ID NO 15
<211> LENGTH: 21
<212> TYPE: DNA
<213> ORGANISM: Artificial
<220> FEATURE:
<223> OTHER INFORMATION: serD GENE FOR PCR PRIMER

<400> SEQUENCE: 15
atcggatccg tctcgagtac t                                               21

<210> SEQ ID NO 16
<211> LENGTH: 17
<212> TYPE: DNA
<213> ORGANISM: Artificial
<220> FEATURE:
<223> OTHER INFORMATION: serD GENE FOR PCR PRIMER

<400> SEQUENCE: 16
caggaaacag atatgac                                                    17

<210> SEQ ID NO 17
<211> LENGTH: 20
<212> TYPE: DNA
<213> ORGANISM: Artificial
<220> FEATURE:
<223> OTHER INFORMATION: serD GENE FOR PCR PRIMER

<400> SEQUENCE: 17
gctagtactc gaaacggatc                                                 20

<210> SEQ ID NO 18
<211> LENGTH: 91
<212> TYPE: PRT
<213> ORGANISM: Artificial
<220> FEATURE:
<223> OTHER INFORMATION: FRAGMENT FOR RESISTANCE AGAINST DEHYDRATION
      STRESS

<400> SEQUENCE: 18

Met Arg Gly Ser His His His His His His Gly Ser Ile Glu Gly Arg
1               5                   10                  15

Ser Ser Thr Gly Ser Ser Ser Asn Thr Asp Ser Asn Ser Asn Ser Ala
            20                  25                  30

Gly Ser Ser Thr Ser Gly Gly Ser Thr Tyr Gly Tyr Ser Ser Asn
        35                  40                  45

Ser Arg Asp Gly Ser Val Ser Ser Thr Gly Ser Ser Ser Asn Thr Asp
    50                  55                  60

Ser Asn Ser Asn Ser Ala Gly Ser Ser Thr Ser Gly Gly Ser Ser Thr
65                  70                  75                  80

Tyr Gly Tyr Ser Ser Asn Ser Arg Gly Ser Val
                85                  90

<210> SEQ ID NO 19
<211> LENGTH: 191
<212> TYPE: PRT
<213> ORGANISM: Artificial
```

```
<220> FEATURE:
<223> OTHER INFORMATION: FRAGMENT FOR RESISTANCE AGAINST DEHYDRATION
      STRESS

<400> SEQUENCE: 19

Met Arg Gly Ser His His His His His Gly Ser Ala Cys Glu Leu
1               5                   10                  15

His Arg Gly Gly Gly Ala Ser Ser Met Thr Gly Gly Gln Gln Met Gly
            20                  25                  30

Arg Gly Ser Ile Glu Gly Arg Ser Ser Thr Gly Ser Ser Ser Asn Thr
            35                  40                  45

Asp Ser Asn Ser Asn Ser Ala Gly Ser Ser Thr Ser Gly Gly Ser Ser
    50                  55                  60

Thr Tyr Gly Tyr Ser Ser Asn Ser Arg Asp Gly Ser Val Ser Ser Thr
65                  70                  75                  80

Gly Ser Ser Ser Asn Thr Asp Ser Asn Ser Asn Ser Ala Gly Ser Ser
                85                  90                  95

Thr Ser Gly Gly Ser Ser Thr Tyr Gly Tyr Ser Ser Asn Ser Arg Asp
            100                 105                 110

Gly Ser Val Ser Ser Thr Gly Ser Ser Ser Asn Thr Asp Ser Asn Ser
            115                 120                 125

Asn Ser Ala Gly Ser Ser Thr Ser Gly Gly Ser Ser Thr Tyr Gly Tyr
    130                 135                 140

Ser Ser Asn Ser Arg Asp Gly Ser Val Ser Ser Thr Gly Ser Ser Ser
145                 150                 155                 160

Asn Thr Asp Ser Asn Ser Asn Ser Ala Gly Ser Ser Thr Ser Gly Gly
                165                 170                 175

Ser Ser Thr Tyr Gly Tyr Ser Ser Asn Ser Arg Asp Gly Ser Val
            180                 185                 190

<210> SEQ ID NO 20
<211> LENGTH: 266
<212> TYPE: PRT
<213> ORGANISM: Artificial
<220> FEATURE:
<223> OTHER INFORMATION: FRAGMENT FOR RESISTIANCE AGAINST DEHYDRATION
      STRESS

<400> SEQUENCE: 20

Met Arg Gly Ser His His His His His Gly Ser Ala Cys Glu Leu
1               5                   10                  15

His Arg Gly Gly Gly Arg Ser Ser Met Thr Gly Gly Gln Gln Met Gly
            20                  25                  30

Arg Gly Ser Ile Glu Gly Arg Ser Ser Thr Gly Ser Ser Ser Asn Thr
            35                  40                  45

Asp Ser Asn Ser Asn Ser Ala Gly Ser Ser Thr Ser Gly Gly Ser Ser
    50                  55                  60

Thr Tyr Gly Tyr Ser Ser Asn Ser Arg Asp Gly Ser Val Ser Ser Thr
65                  70                  75                  80

Gly Ser Ser Ser Asn Thr Asp Ser Asn Ser Asn Ser Ala Gly Ser Ser
                85                  90                  95

Thr Ser Gly Gly Ser Ser Thr Tyr Gly Tyr Ser Ser Asn Ser Arg Asp
            100                 105                 110

Gly Ser Val Ser Ser Thr Gly Ser Ser Ser Asn Thr Asp Ser Asn Ser
            115                 120                 125

Asn Ser Ala Gly Ser Ser Thr Ser Gly Gly Ser Ser Thr Tyr Gly Tyr
    130                 135                 140
```

```
Ser Ser Asn Ser Arg Asp Gly Ser Val Ser Thr Gly Ser Ser Ser
145                 150                 155                 160

Asn Thr Asp Ser Asn Ser Asn Ser Ala Gly Ser Ser Thr Ser Gly Gly
                165                 170                 175

Ser Ser Thr Tyr Gly Tyr Ser Ser Asn Ser Arg Asp Gly Ser Val Ser
                180                 185                 190

Ser Thr Gly Ser Ser Ser Asn Thr Asp Ser Asn Ser Asn Ser Ala Gly
                195                 200                 205

Ser Ser Thr Ser Gly Gly Ser Thr Tyr Gly Tyr Ser Ser Asn Ser Arg
    210                 215                 220

Asp Gly Ser Val Ser Ser Thr Gly Ser Ser Ser Asn Thr Asp Ser Asn
225                 230                 235                 240

Ser Asn Ser Ala Gly Ser Ser Thr Ser Gly Gly Ser Thr Tyr Gly
                245                 250                 255

Tyr Ser Ser Asn Ser Arg Asp Gly Ser Val
                260                 265

<210> SEQ ID NO 21
<211> LENGTH: 343
<212> TYPE: PRT
<213> ORGANISM: Artificial
<220> FEATURE:
<223> OTHER INFORMATION: FRAGMENT FOR RESISTANCE AGAINST DEHYDRATION

<400> SEQUENCE: 21

Met Arg Gly Ser His His His His His Gly Ser Ala Cys Glu Leu
1               5                   10                  15

His Arg Gly Gly Gly Arg Ser Ser Met Thr Gly Gly Gln Gln Met Gly
                20                  25                  30

Arg Gly Ser Ile Glu Gly Arg Ser Ser Thr Gly Ser Ser Ser Asn Thr
                35                  40                  45

Asp Ser Asn Ser Asn Ser Ala Gly Ser Ser Thr Ser Gly Gly Ser Ser
    50                  55                  60

Thr Tyr Gly Tyr Ser Ser Asn Ser Arg Asp Gly Ser Val Ser Ser Thr
65                  70                  75                  80

Gly Ser Ser Ser Asn Thr Asp Ser Asn Ser Asn Ser Ala Gly Ser Ser
                85                  90                  95

Thr Ser Gly Gly Ser Ser Thr Tyr Gly Tyr Ser Ser Asn Ser Arg Asp
                100                 105                 110

Gly Ser Val Ser Ser Thr Gly Ser Ser Ser Asn Thr Asp Ser Asn Ser
                115                 120                 125

Asn Ser Ala Gly Ser Ser Thr Ser Gly Gly Ser Ser Thr Tyr Gly Tyr
    130                 135                 140

Ser Ser Asn Ser Arg Asp Gly Ser Val Ser Ser Thr Gly Ser Ser Ser
145                 150                 155                 160

Asn Thr Asp Ser Asn Ser Asn Ser Ala Gly Ser Ser Thr Ser Gly Gly
                165                 170                 175

Ser Ser Thr Tyr Gly Tyr Ser Ser Asn Ser Arg Asp Gly Ser Val Ser
                180                 185                 190

Ser Thr Gly Ser Ser Ser Asn Thr Asp Ser Asn Ser Asn Ser Ala Gly
                195                 200                 205

Ser Ser Thr Ser Gly Gly Ser Ser Thr Tyr Gly Tyr Ser Ser Asn Ser
    210                 215                 220

Arg Asp Gly Ser Val Ser Ser Thr Gly Ser Ser Ser Asn Thr Asp Ser
225                 230                 235                 240
```

-continued

```
Asn Ser Asn Ser Ala Gly Ser Ser Thr Ser Gly Gly Ser Ser Thr Tyr
            245                 250                 255

Gly Tyr Ser Ser Asn Ser Arg Asp Gly Ser Val Ser Ser Thr Gly Ser
            260                 265                 270

Ser Ser Asn Thr Asp Ser Asn Ser Asn Ser Ala Gly Ser Ser Thr Ser
            275                 280                 285

Gly Gly Ser Ser Thr Tyr Gly Tyr Ser Ser Asn Ser Arg Asp Gly Ser
        290                 295                 300

Val Ser Ser Thr Gly Ser Ser Ser Asn Thr Asp Ser Asn Ser Asn Ser
305                 310                 315                 320

Ala Gly Ser Ser Thr Ser Gly Gly Ser Ser Thr Tyr Gly Tyr Ser Ser
            325                 330                 335

Asn Ser Arg Asp Gly Ser Val
            340
```

METHOD OF PREVENTING DECREASE IN THE ACTIVITY OF PROTEIN DUE TO FREEZING AND USE OF POLYPEPTIDE IN THE PRODUCTION OF PROTEIN ACTIVITY DECREASE PREVENTING AGENT

BACKGROUND OF THE INVENTION

1. Field of the Invention

The present invention relates to a method for protecting proteins from denaturation which occurs when the proteins are frozen. Further, the present invention is relates to use of polypeptides for protecting proteins from such denaturation caused by freezing.

2. Description of the Prior Art

In the field of genetic engineering, biochemistry, food and pharmaceutical industries, and the like, various proteins including enzymes are commonly preserved by freezing.

Generally, proteins are known to change their high-dimensional structure upon freezing and thawing. When such denaturation of proteins associated with the freezing (occasionally called freeze denaturation hereinafter) occurs, protein activity may be decreased or completely lost, which causes problems in storing proteins.

Conventionally, in order to prevent such freeze denaturation of proteins, bovine serum albumin (BSA), glycerol, sugars, or the like are usually added to the proteins to be kept frozen for storage.

However, when the abovementioned additives are used, bovine serum albumin (BSA) is limited in its supply and generally very expensive. Further, serums derived from animals cannot sufficiently ensure the safety because of their possible risk of viral infection. Furthermore, glycerol, sugars or the like must be added at a concentration as high as 20% or so, which affects activity of proteins of interest. Further in this case, a process to remove the abovementioned additives may be required after freezing and thawing depending on the kind of proteins or use thereof, which may require a complicated removing step or may increase the cost. Also for this reason, use of these additives has not been desirable.

Accordingly, there is still a need for means to prevent freeze-induced decrease in protein activity or inactivation of proteins during freezing/thawing cycles.

SUMMARY OF THE INVENTION

The present inventors have recently found that polypeptides having a specific amino acid repeat sequence are effective in the prevention of decrease in activity or inactivation of proteins, such as enzymes, associated with freeze denaturation. The present invention is based on this finding.

Accordingly, an objective of the present invention is to provide a means to prevent freeze-induced decrease in protein activity.

Further, a method according to the present invention is a process for preventing freeze-induced decrease in protein activity comprising adding a polypeptide comprising the following amino acid sequence (I) to a protein to be frozen:

```
                                    (SEQ ID NO: 1)
Ser-Ser-Thr-Gly-Ser-X1-Ser-X2-Thr-Asp-X3-X4-X5-X6-
-continued
X7-X8-Gly-Ser-X9-Thr-Ser-Gly-Gly-Ser-Ser-Thr-Tyr- Gly-Tyr-Ser-Ser-X10-X11-X12-X13-Gly-X14-Val  (I)
``` wherein,

X1 represents Ser or Thr,

X2 represents Asn or Thr,

X3 represents Ser or Ala,

X4 represents Asn or Ser,

X5 represents Ser or Thr,

X6 represents Asn, Asp, or Lys,

X7 represents Ser, Asn, or Lys,

X8 represents Ala, Thr, or Val,

X9 represents Ser, or Arg,

X10 represents Asn, Ser, Asp, or Arg,

X11 represents Ser, Asn, His, or Cys,

X12 represents Arg or Gly,

X13 represents Asp or Gly, and

X14 represents Ser or Arg.

Further, the present invention provides use of a polypeptide comprising the abovementioned amino acid sequence (I) to produce an agent for preventing freeze-induced decrease in protein activity.

According to the method of the present invention, decrease in protein activity during freezing/thawing of proteins such as enzymes can be prevented, stability of proteins during storage can be improved, and the range of application of the proteins after storage by freezing can be extended. The method according to the present invention is extremely useful in the field of food industry, pharmaceutical industry, and the like.

DETAILED DESCRIPTION OF THE INVENTION

Figure 1:
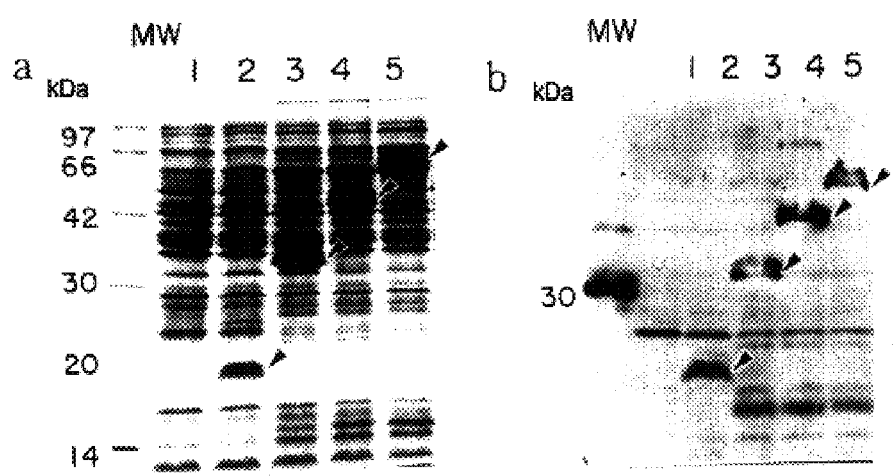
FIG. 1 shows photographs demonstrating the result of Coomassie staining and the result of detection of histidine tags by Ni-NTA, which confirms the production of SP by gene expression in *Escherichia coli*.

A process for preventing freeze-induced decrease in protein activity according to the present invention comprises adding a polypeptide comprising the abovementioned amino acid sequence (I) to a protein to be frozen. In the abovementioned amino acid sequence (I), X1 to X14 independently represent as follows:

X1 represents Ser or Thr, preferably Ser,

X2 represents Asn or Thr, preferably Asn,

X3 represents Ser or Ala, preferably Ala,

X4 represents Asn or Ser, preferably Asn,

X5 represents Ser or Thr, preferably Ser,

X6 represents Asn, Asp, or Lys, preferably Asn,

X7 represents Ser, Asn, or Lys, preferably Asn

X8 represents Ala, Thr, or Val, preferably Ala

X9 represents Ser, or Arg, preferably Ser,

X10 represents Asn, Ser, Asp, or Arg, preferably Asn,

X11 represents Ser, Asn, His, or Cys, preferably Ser,

X12 represents Arg or Gly, preferably Arg,

X13 represents Asp or Gly, preferably Asp, and

X14 represents Ser or Arg, preferably Ser.

In the present invention, said polypeptide can further comprise a homologue of the abovementioned amino acid sequence (I). The term "homologue" herein used means a polypeptide having an amino acid sequence of the abovementioned amino acid sequence (I) in which one or more (preferably one or several) amino acids are deleted, substituted, inserted, or added, still having a function for preventing freeze-induced decrease (or inactivation) in protein activity (occasionally referred to as cryoprotective activity in this specification).

In a preferred embodiment of the present invention, the abovementioned amino acid sequence (I) is preferably the following amino acid sequence (II), namely said polypeptide according to the present invention preferably comprises the following amino acid sequence (II):

(SEQ ID NO: 2)
Ser-Ser-Thr-Gly-Ser-Ser-Ser-Asn-Thr-Asp-Ser-

Asn-Ser-Asn-Ser-Ala-Gly-Ser-Ser-Thr-Ser-Gly-

Gly-Ser-Ser-Thr-Tyr-Gly-Tyr-Ser-Ser-Asn-Ser-

Arg-Asp-Gly-Ser-Val (II)

Said polypeptide according to the present invention can typically prevent protein denaturation, typically decrease in protein activity caused by freezing that may occur upon freezing of a protein of interest, when added to said protein of interest.

The term "preventing freeze-induced decrease in protein activity" herein means preventing decrease in protein activity or inactivation of proteins that may be caused when a protein of interest is frozen or frozen and thawed. The term also implies maintaining activity of said protein, stabilizing said protein, and preventing protein denaturation.

In the present invention, "freezing" proteins typically means that proteins are maintained under usual freezing storage conditions, for example, in refrigeration below 0° C.

In the present invention, proteins of to be frozen are not particularly restricted and can be any proteins as long as their activity is decreased or lost by freezing. In the present invention, preferable examples of such proteins are enzymes. Examples of such enzymes include those important in industry, such as proteases, amylases, cellulases, lipases, restriction enzymes, and modification enzymes.

Furthermore, the present invention also provides use of a polypeptide comprising the abovementioned amino acid sequence (I) for the production of agents for preventing freeze-induced decrease in activity of proteins.

Here, "agents for preventing decrease in activity" are those which can prevent decrease in activity of proteins or inactivation of proteins that may be caused upon freezing or thawing of the proteins of interest. Forms, doses or the like of the agents are not particularly restricted.

Further, the polypeptide comprising the abovementioned amino acid sequence (I) can, if present in a cell, control the stress associated with dehydration of the cell which affects the cell. Namely, said polypeptides can protect the cell from the dehydration stress (occasionally referred to as "protective function against dehydration stress" in this specification). In other words, the polypeptide according to the present invention may further be able to render dehydration stress tolerance to the cell. Examples of such cell (or target cell) include cells of microorganisms such as *Escherichia coli, Bacillus subtilis* and yeast, fungi, insects, animals, and plants.

Thus, according to another embodiment of the present invention, there are provided a process for rendering dehydration stress tolerance to a target cell comprising introducing a polypeptide comprising the amino acid sequence (I) to the target cell for the accumulation therein. Preferably, this process for rendering dehydration stress tolerance to the target cell comprises transforming the target cell using a recombinant vector (to be explained later) comprising a DNA encoding a polypeptide comprising the amino acid sequence (I). Further, in this specification, the terms "DNA" and "gene" may occasionally be used for meaning the same.

According to a preferred embodiment of the present invention, said polypeptide preferably comprises a repetitive sequence in which the abovementioned amino acid sequence (I) is repeated at least twice. Use of the polypeptide having such a repetitive sequence can further improve the effectiveness for preventing decrease in protein activity by the method according to the present invention.

Accordingly, the number of repeat of the amino acid sequence (I) in a polypeptide of the present invention is preferably at least 2. The greater number of repeat is preferable to attain the more remarkable abovementioned effectiveness. However, the number of the repeat is preferably 2 to 8, more preferably 2 to 6, and most preferably 2 to 4, taking possible cost increase due to the complicated repeating process and the compatibility upon the introduction into a cell into consideration.

A polypeptide comprising a repetitive sequence in which the abovementioned amino acid sequence (I) is repeated at least twice can be obtained, for example, as follows:

First, a DNA encoding a repetitive sequence in which the amino acid sequence (I) is repeated twice is designed and then synthesized using an ordinary DNA synthesizer. Here, it is desirable to place restriction enzyme recognition sites on both terminals of the abovementioned sequence to link to a vector and a translation stop codon at the 3' terminal. Further, if it is not desirable to obtain as an entire length of DNA chain considering reliability and operability of a DNA synthesizer or a DNA purification method, segmented fragments may be first prepared and then linked together to obtain the entire length of DNA. In this way, a DNA encoding a repetitive sequence of interest can be obtained. Next, the DNA thus obtained is expressed to obtain a polypeptide, for example, using a method described hereinafter. Thus, a polypeptide comprising a repetitive sequence (for example, the following sequence (III)), in which the amino acid sequence (I) is repeated twice, can be obtained. Amino acid sequence (III):

(SEQ ID NO: 3)
Ser-Ser-Thr-Gly-Ser-Ser-Ser-Asn-Thr-Asp-Ser-Asn-

Ser-Asn-Ser-Ala-Gly-Ser-Ser-Thr-Ser-Gly-Gly-Ser-

Ser-Thr-Tyr-Gly-Tyr-Ser-Ser-Asn-Ser-Arg-Asp-Gly-

Ser-Val-Ser-Ser-Thr-Gly-Ser-Ser-Ser-Asn-Thr-Asp-

Ser-Asn-Ser-Asn-Ser-Ala-Gly-Ser-Ser-Thr-Ser-Gly-

-continued

Gly-Ser-Ser-Thr-Tyr-Gly-Tyr-Ser-Ser-Asn-Ser-Arg-
Asp-Gly-Ser-Val.

The sequence consisting of 38 amino acids of the abovementioned amino acid sequence (I) is hereinafter referred to as "SP" and the polypeptide consisting of two repeats thereof is occasionally called SP2.

Further in the present invention, a DNA encoding SP4 having 4 repetitive SPs can be obtained by obtaining a DNA in which specific restriction enzyme sites are added to both terminals of a DNA encoding SP2 synthesized by the PCR method using specific primers and then linking these restriction enzyme sites using restriction enzymes. Thus, by using the same technique, a DNA encoding SP6, a DNA encoding SP8, and the like can be obtained one by one, and DNAs encoding more repetitive sequences can be obtained in necessary. As described above, DNAs thus obtained can be expressed to obtain polypeptides such as SP4, SP6, and SP8.

A polypeptides comprising a repetitive sequence having at least two repeats of the amino acid sequence (I) can be obtained in such a manner as described above; however, alternatively, the abovementioned polypeptide of interest can be obtained by first obtaining more than one polypeptides having the amino acid sequence (I) using, for example, the method described hereinafter and then linking them one another using a conventional chemical method.

In the present invention, a polypeptide comprising the abovementioned amino acid sequence (I) can either be produced using various conventional synthesis methods or be derived from nature. As the amino acid sequence of this polypeptide has been determined, it can be obtained by synthesizing its whole sequence, or partially using a sequence derived from nature and further synthesizing based on the sequence.

According to a preferred embodiment of the present invention, said polypeptide can be derived from a natural protein, sericin, and accordingly be obtained from this sericin using conventional genetic engineering. Natural sericin can be obtained, for example, from silk gland tissue of silkworm, cocoons, or raw silk. In the present invention, sericin implies hydrolysis products of this protein in addition to sericin itself.

Further, in the present invention, in cases where a DNA encoding a polypeptide comprising the abovementioned amino acid sequence (I) is available or can be produced, the polypeptide can be produced in a transformed cell obtained by transforming a host cell with this DNA. More specifically, a polypeptide according to the present invention can be produced by culturing a transformant obtained by transforming a host cell using a DNA, in particular a recombinant vector, which contains a DNA fragment encoding said polypeptide according to the present invention in a form amplifiable and replicable in the host cell. Namely, in the present invention, what is called a host-vector system can be used for producing said polypeptide. In the present invention, upon applying such a host-vector system, various methods commonly used in this field for the construction of expression vectors (recombinant vectors) and the transformation can be used.

Thus, according to another preferred embodiment of the present invention, the abovementioned polypeptide is obtained by a method comprising:

preparing a recombinant vector comprising a DNA encoding a polypeptide comprising the amino acid sequence (I), obtaining a transformed cell by transforming a cell using said recombinant vector, culturing said transformed cell, and recovering a polypeptide from the resulting cells and/or culture thereof.

In the present invention, a DNA containing a gene encoding the abovementioned polypeptide, particularly a recombinant vector, can be obtained by incorporating a DNA fragment encoding the abovementioned polypeptide into a commonly used vector system. In the present invention, it is preferable that this vector contains the encoding DNA fragment in a repetitive form as mentioned above.

A vector to be used in the present invention can be selected from commonly used vectors in which a host-vector system is established, such as plasmids, viruses, phages, and cosmid vectors, depending on the kind of a host cell to be used. More specifically, for example, a pBR-, pUC- or pQE-based plasmid, or λ-phage bacteriophage is used when *Escherichia coli* is a host cell, a pUB-based plasmid is used when *Bacillus subtilis* is a host cell, and a YEp- or YCp-based vector is used when yeast is a host cell. A vector to be used in the present invention is preferably a plasmid.

A plasmid usable in the present invention preferably contains a marker for selecting a transformant. Examples of such marker include genes conferring resistance to drugs, such as ampicillin and kanamycin, and genes complementing a nutritional requirement. Further, in the present invention, restoration of β-galactosidase activity by a specific peptide generated by a vector DNA such as a plasmid and a peptide encoded in a host cell can also be used as a selection marker.

Further in the present invention, a DNA to be used as said recombinant vector preferably has DNAs necessary for expressing a polypeptide comprising the abovementioned amino acid sequence (I), such as a promoter, transcription start signal, translation stop signal, transcription control signal such as transcription termination signal, and translation control signal.

The present invention provides a transformant obtained by transforming a host cell with the abovementioned recombinant vector.

In the present invention, any host cell can be used as long as its host-vector system is established. Examples of such host cell include *Escherichia coli, Bacillus subtilis*, yeasts and fungi.

When a host cell is *Escherichia coli, Bacillus subtilis*, yeast or fungus, a secretion vector that extracellularly secretes the abovementioned polypeptide of interest can be used as a vector.

According to still another embodiment of the present invention, the abovementioned polypeptide can be a chimeric protein in which a polypeptide comprising the abovementioned amino acid sequence (I) and a heterologous polypeptide (for example, another functional protein) are hybridized.

A chimeric protein can be produced by expressing a DNA encoding the chimeric protein made by DNA fusion using a DNA encoding a polypeptide comprising the abovementioned amino acid sequence (I) and a DNA encoding a heterologous polypeptide.

EXAMPLE

The present invention is further illustrated by the following examples that are not intended as a limitation of the invention.

Chemical Synthesis of Gene Fragments Encoding a Polypeptide having Cryoprotective Activity A gene (hereinafter called serD) encoding a polypeptide consisting of the abovementioned amino acid sequence of SP2 (the abovementioned sequence (III) (SEQ ID NO: 3)) was designed. Here, a recognition site (Ile-Glu-Gly-Arg) for protease (Factor Xa) was located at the N-terminal of SP2 to cleave another fused polypeptide. Furthermore, the above-mentioned gene was designed, taking the codon usage frequency of *Escherichia coli* (Ikemura, T. and Ozeki, H., Cold Spring Harbor Symp. Quant. Biol., 47, 1087(1983)) into consideration, to locate restriction enzyme recognition sites (PstI, EcoRI) for the linkage to a vector at both terminals (5' and 3' terminals) of serD and to add two translation stop codons at the 3' terminal side.

Next, the designed gene was chemically synthesized using phosphoramidite chemistry on a DNA synthesizer (Applied Biosystems). In this case, taking reliability and operability of current DNA synthesizers and DNA purification methods into consideration, the DNA was synthesized as divided fragments each having about 60 to 70 bases.

Said repetitive unit SP is consisted of 38 amino acid residues, namely 114 bases. Taking stability of gene products, a DNA encoding SP2 (serD) in which a repetitive unit of 38 amino acid residues is repeated twice is used as a base unit of synthesized DNA. Therefore, a gene of at least 228 bases is necessary. Furthermore, since the DNA has to be incorporated as a double-stranded chain, twice the amount of DNA has to be synthesized.

In practice, the introduction of stop codons and the restriction enzyme sites for linkage of each fragment to a plasmid are also necessary for the synthetic gene encoding SP2. Therefore the entirety of gene encoding SP2 was divided into 4 fragments, so that 4 front-and-back pairs, i.e., the total of 8, of DNA chains were synthesized.

The 8 DNA fragments synthesized are as follows:

complementary sequence portion to obtain four double-stranded DNA fragments constructing serD.

Further, the 5' terminal of the synthesized gene fragment was phosphorylated using T4 polynucleotide kinase, since no phosphoric was present at the 5' terminal of the DNA encoding the oligonucleotide obtained by the chemical synthesis.

Namely, the following components were placed into a tube (manufactured by Eppendolf Co.), reacted at 37° C. for 1 hour, and then heated at 70° C. for 5 minutes to inactivate the enzyme.

| | |
|---|---|
| Individual oligonucleotide 100 pmole (in water) | 7.5 μl |
| 10 × buffer* | 1 μl |
| 10 mM ATP | 1 μl |
| T4 polynucleotide kinase (Takara Shuzo Co., Ltd.) | 10 μl |
| 0.5 μl (5 units) | |

*[10 × buffer: 650 nM Tril-HCl (pH 7.6), 100 mM MgCl$_2$, 150 nM dithiothreitol, 10 mM spermidine].

A 5 μl portion of each of the DNAs was mixed in a tube (manufactured by Eppendolf Co.) and reacted for linkage at 16° C. for 30 minutes using a Takara ligation kit version II (Takara Shuzo Co., Ltd.) to adjacently link the four DNA fragments. After the reaction, agarose gel electrophoresis was carried out and a DNA fragment of about 270 bp was recovered from the gel. The resulting DNA fragment had a PstI recognition site at the 5' terminal and an EcoRI recognition site at the 3' terminal.

Further, said DNA fragment was mixed with an appropriate amount of plasmid pUC19 (Yanisch-Perron, C. et al, Gene, 33, 103(1985))previously cleaved with PstI and

```
serD fragment (1)
5'-GTGATCAATCGAAGGTCGCTCGAGTACTGGTTCTTCTTCTAACACCGACTCTAACT    (SEQ ID NO: 4)
CTAAC-3' serD fragment (2)
5'-TCTGCTGGTTCTTCTACCTCTGGTGGTTCTTCTACCTACGGTTACTCTTCTAACT    (SEQ ID NO: 5)
CTCGTGACGGTTCT-3' serD fragment (3)
5'-GTTTCTTCTACCGGTTCTTCTTCTAACACCGACTCTAACTCTAACTCTGCTGGTT    (SEQ ID NO: 6)
CTTCTACCTC-3' serD fragment (4)
5'-TGGTGGTTCTTCTACCTACGGTTACTCTTCTAACTCTCGTGACGGATCCGTTTAA    (SEQ ID NO: 7)
TAGCTGAGCG-3' serD fragment (1')
5'-CAGAGTTAGAGTTAGAGTCGGTGTTAGAAGAAGAACCAGTACTCGAGCGACCTTC    (SEQ ID NO: 8)
GATTGATCACTGCA-3' serD fragment (2')
5'-AAACAGAACCGTCACGAGAGTTAGAAGAGTAACCGTAGGTAGAAGAACCACCAGA    (SEQ ID NO: 9)
GGTAGAAGAACCAG-3' serD fragment (3')
5'-ACCAGAGGTAGAAGAACCAGCAGAGTTAGAGTTAGAGTCGGTGTTAGAAGAAGAA    (SEQ ID NO: 10)
CCGGTAGAAG-3' serD fragment (4')
5'-AATTCGCTCAGCTATTAAACGGATCCGTCACGAGAGTTAGAAGAGTAACCGTAGG    (SEQ ID NO: 11)
TAGAAGAACC-3'
```

Construction of Gene (serD) Encoding SP2

The eight fragments (about 70 bp) synthesized as mentioned above were made into double-stranded chains by an annealing process with fragments having each other a EcoRI, and ligation reaction was carried out at 16° C. for 1 hour using a Takara ligation kit version II (Takara Shuzo Co., Ltd.).

Next, the resulting reaction mixture was introduced into *Escherichia coli* strain JM109 (recA1,Δlac-proAB, endA1, gryA96, thi-1, hsdR17, supE44, relA1, λ⁻, (F'traD36, proAB, lacI q Z ΔM15)).

Further, this *E. coli* strain JM109 is a strain in which upon transformation of pUC-based plasmid DNA or transduction of M13 phage vector DNA, a lacZα peptide generated from the vector DNA and lacZΔM15 encoded by JM109F' restore β-galactosidase activity, which facilitates a selection of recombinants.

Accordingly, in a medium containing IPTG (isopropyl-β-D-thiogalactopyranoside) and X-Gal (5-bromo-4-chloro-3-indole-β-D-galactoside), cells of this strain JM109 carrying plasmid pUC19 form blue colonies showing β-galactosidase activity. On the other hand, since β-galactosidase activity cannot be restored in strain JM109 carrying a recombinant plasmid in which a foreign DNA fragment is inserted, cells of this strain form white colonies. The recombinant plasmids can thereby be selected.

Accordingly, plasmids were prepared from white colonies formed and subjected to DNA sequencing (Sanger, F. et al, J. Mol. Biol., 143, 161 (1980)) to select a clone having a serD base sequence (fragment) exactly the same as designed.

The recombinant plasmid having the serD gene thus obtained is herein called pUC-serD.

Polymerization of SP

Polymerization of SP was carried out as follows.

pET-serD

A fragment containing serD obtained by cleaving the abovementioned pUC-serD with BclI and Bpu1102I was mixed with vector pET3a (Novagen) previously cleaved with restriction enzymes BamHI and Bpu1102I, and ligation reaction was carried out at 16° C. for 1 hour using a Takara ligation kit version II (Takara Shuzo Co., Ltd.).

Next, the resulting reaction mixture was introduced into *E. coli* strain JM109 as described above. A plasmid was prepared from a transformant thus obtained, subjected to DNA sequencing and then confirmed to have the sequence of serD.

The recombinant plasmid having the serD gene thus obtained is herein called pET-serD.

pET-serT

Next, a serD gene having XhoI sites added at both terminals of the synthesized serD gene for SP2 was obtained by the PCR method. The PCR reaction was carried out by an ordinary method using an Ex Taq (Takara Shuzo Co., Ltd.). Primers used herein are as follows:

```
5'-AAGGTCGCTCGAGTACCGGT-3'   (SEQ ID NO: 12)

5'-CGCTCAGACTCGAGACAGAT-3'   (SEQ ID NO: 13)
```

Next, the serD gene having the added XhoI sites at both terminals was linked to the XhoI site of pET-serD utilizing the restriction enzyme sites to construct plasmid pET-serT having a gene encoding SP4 consisting of 4 repetitive SPs.

pET-serH

Similarly, a serD gene in which a BamHI site was added to the 5' terminal was obtained by the PCR method.

By utilizing the restriction enzyme sites, the resulting serD was linked to the BamHI site of pET-serT to construct plasmid pET-serH having a gene encoding SP6 consisting of 6 repetitive SPs.

Primers herein used for introducing the BamHI site into the serD gene are as follows:

```
5'-GTTTTCCCAGTCACGAC-3'      (SEQ ID NO: 14)

5'-ATCGGATCCGTCTCGAGTACT-3'  (SEQ ID NO: 15)
``` pET-serO

Similarly, a serD gene in which a ScaI site was added to the 3' terminal was obtained by the PCR method.

By utilizing the restriction enzyme sites, the resulting serD was linked to the ScaI site of pET-serH to construct plasmid pET-serO having a gene encoding SP8 consisting of 8 repetitive SPs.

Primers herein used for introducing the ScaI site into the serD gene are as follows:

```
5'-CAGGAAACAGATATGAC-3'      (SEQ ID NO: 16)

5'-GCTAGTACTCGAAACGGATC-3'   (SEQ ID NO: 17)
```

Construction of Expression Plasmid for *E. coli*
Construction of pQE-NHserD

A fragment containing serD obtained by cleaving pUC-serD with PstI and EcoRI was mixed with plasmid pBSIISK+ previously cleaved with PstI and EcoRI, and ligation reaction was carried out at 16° C. for 1 hour using a Takara ligation kit version II (Takara Shuzo Co., Ltd.).

Next, the resulting reaction mixture was introduced into *E. coli* strain JM109 as described above. A plasmid was prepared from a transformant thus obtained, from which it was confirmed that the serD gene (about 270 bp) was properly inserted.

The recombinant plasmid having the serd gene thus obtained is herein called pBS-serD.

Next, a fragment containing serD obtained by cleaving pBS-serD with BclI and HindIII was mixed with a high-level expression vector pQE30 for *E. coli* (Qiagen) previously cleaved with BclI and HindIII, and ligation reaction was carried out at 16° C. for 1 hour using a Takara ligation kit version II (Takara Shuzo Co., Ltd.).

Next, the resulting reaction mixture was introduced into *E. coli* strain JM109 as described above.

A plasmid was prepared from a transformant thus obtained, from which it was confirmed that the serD gene (about 270 bp) was properly inserted.

The recombinant plasmid having the serD gene thus obtained is herein called pQE-NHserD.

Here, a 6×His tag was designed to be located at the N-terminal of SP2. The amino acid sequence of the expressed polypeptide is shown in SEQ ID NO: 18.

Construction of pQE-NHLserT, pQE-NHLserH, and pQE-NHLserO

The abovementioned plasmids pET-serT, pET-serH, and pET-serO were cleaved with NheI to obtain fragments containing serT, serH, and serO, and these fragments were each linked to the XbaI site of PBSIISK+ to construct recombinant plasmids. These recombinant plasmids were then cleaved with ScaI and HindIII to prepare fragments containing genes serT, serH, and serO encoding SP4, SP6, and SP8, respectively. The gene fragments thus prepared were each linked to a high-level expression vector pQE30 for *E. coli* to construct individual expression plasmids pQE-NHLserT, pQE-NHLserH and pQE-NHLserO.

Here, 6×His tags were designed to be located at the N-terminals of SP4, SP6, and SP8.

The amino acid sequences of the expressed polypeptides are shown in SEQ ID NO: 19, SEQ ID NO: 20, and SEQ ID NO: 21.

Induction and Confirmation of Expression of Gene Encoding SP in E. coli

Preparation of E. coli Transformant

Expression vectors pQE-NHserD, pQE-NHLserT, pQE-NHLserH, and pQE-NHLserO, into which genes encoding SPs were incorporated, and the sole vector pQE as a control were each introduced into E. coli strain JM109 (recA1,ΔlacproAB, endA1, gryA96, thi-1, hsdR17, supE44, relA1, λ⁻, (F'traD36, proAB, lacI q Z ΔM15)). Since the expression vector pQE for E. coli carries an ampicillin resistance gene as a selection marker, transformants were selected as ampicillin resistant colonies.

Induction of Expression

E. coli JM109 transformants each carrying an expression plasmid into which a gene encoding SP was incorporated were cultured in a M9+2% casamino acid medium supplemented with 50 μg/ml ampicillin at 37° C. overnight with shaking. The resulting culture was inoculated into the same medium at a concentration of 2%, and cultivation was continued at 37° C. with shaking.

IPTG (isopropyl β-D-thiogalactopyranoside) was added to the culture thus obtained at a final concentration of 1 mM when the absorbance at 610 nm reached 0.3 to 0.5, and the cultivation was continued for 4 hours.

Confirmation of Expression

After cultivation, the culture supernatant was removed by centrifugation, and the resulting cells were resuspended in a buffer solution [50 mM Na-phosphate(pH7.8), 300 mM NaCl] of 1/10 the volume of the culture medium. Then, the cells were ruptured by sonication (200W, about 30 minutes) to prepare a cell-free extract.

A portion of the cell-free extract was subjected to SDS-polyacrylamide gel electrophoresis by an ordinary method. Coomassie staining of the resulting gel confirmed the expressed SP as a thick band.

Further, the SDS-polyacrylamide gel electrophoresis pattern was transferred to a nitrocellulose membrane, after which the histidine hexamer (6×His) tag added to the N-terminal side of SP was detected by chemical color reaction using HRP-labeled Ni-NTA (nitrilotriacetic acid) (Qiagen), and thus the production of targeted SP was confirmed.

Further, the result of N-terminal amino acid sequencing of the peptide using Edman degradation confirmed that it had the amino acid sequence as designed.

The results of the abovementioned Coomassie staining and histidine tag detection by Ni-NTA are shown in FIG. 1.

Purification of SP

Since peptides produced by expression are highly hydrophilic and virtually do not form high-dimensional structure, they are not precipitated by treating at 100° C. for 10 minutes. By utilizing this property, the cell-free extract prepared by sonication was treated at 100° C. for 10 minutes and then centrifuged at 6,500 rpm for 5 minutes to precipitate denatured proteins derived from E. coli and recover SP from the supernatant as a soluble fraction.

Next, SP was purified from the supernatant of the cell-free extract using QIAexpress Ni-NTA Protein Purification System (Qiagen). This QIAexpress Ni-NTA Protein Purification System can purify a protein having a histidine hexamer (6×His) tag utilizing its high affinity with Ni-NTA (nitrilotriacetic acid).

Test for Evaluating Cryoprotective Activity on Enzyme

Preparation of SP

An E. coli JM109 transformant carrying an expression plasmid (pQE-NHserD) into which a gene encoding SP was incorporated was cultured in a M9+2% casamino acid liquid medium supplemented with 50 μg/ml ampicillin at 37° C. overnight with shaking. Next, the resulting culture was inoculated into the same medium at a concentration of 2%, and cultivation was continued at 37° C. with shaking.

IPTG (isopropyl β-D-thiogalactopyranoside) was added at a final concentration of 1 mM when the absorbance at 610 nm reached 0.3 to 0.5 to induce gene expression, and the cultivation was continued for 4 hours.

After cultivation, the culture supernatant was removed by centrifugation, and the resulting cells were resuspended in a buffer solution [50 mM Na-phosphate (pH7.8), 300 mM NaCl] of 1/10 the volume of the culture medium. Then, the cells were ruptured by sonication (200W, about 30 minutes) to prepare a cell-free extract.

Using a portion of the cell-free extract, SDS-polyacrylamide gel electrophoresis and Coomassie staining was carried out according to ordinary methods to confirm SP expression.

Utilizing the abovementioned property of SP produced by expression, the cell-free extract prepared by sonication was treated by heating at 100° C. for 10 minutes and then centrifuged at 6,500 to 12,000 rpm for 5 to 20 minutes to precipitate denatured proteins derived from E. coli and recover SP from the supernatant as a soluble fraction.

Next, SP contained in the supernatant after heat treatment was further purified using QIAexpress Ni-NTA Protein Purification System (Qiagen). In this QIAexpress Ni-NTA Protein Purification System, a protein having a histidine hexamer (6×His) tag is absorbed utilizing high affinity with Ni-NTA (nitrilotriacetic acid) and then eluted with a 0.02–1.0 M imidazole solution.

Figure 2:
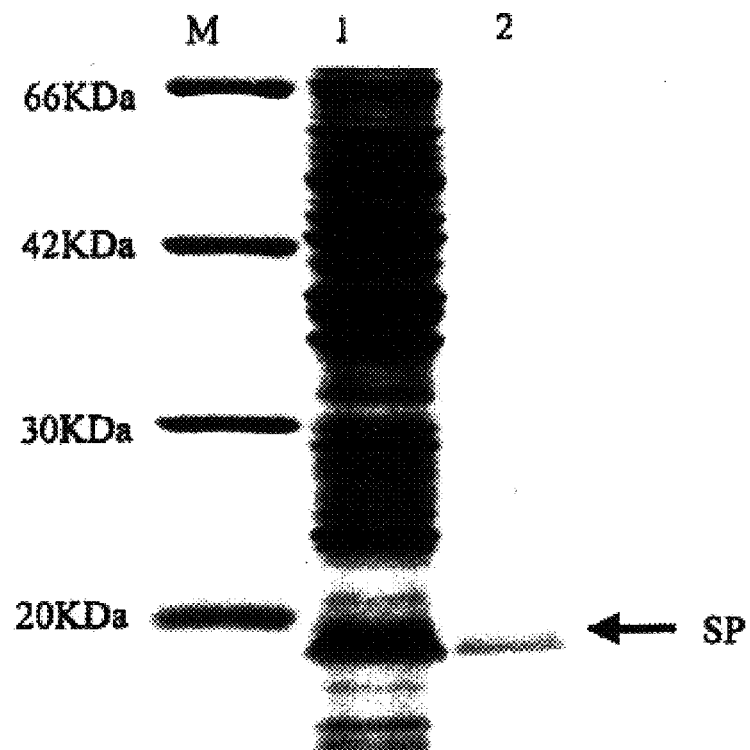
FIG. 2 shows a photograph of the result for confirming the purity of SP produced by expression in *Escherichia coli*.

The purified SP was confirmed by SDS-polyacrylamide gel electrophoresis and Coomassie staining (FIG. 2). Further, the SP concentration was measured by the BCA method extensively used for protein quantification.

Evaluation Test (Cryoprotective Activity on LDH)

SP produced by the expression in E. coli was measured for protective activity against loss of enzymatic activity caused by freezing/thawing.

Lactate dehydrogenase (LDH) was used as a model enzyme. Lactate dehydrogenase (LDH) is an enzyme that acts in a process of producing L-lactic acid from pyruvic acid in a glycolytic pathway. LDH is known to be highly sensitive to freezing stress and tend to lose its activity by freezing/thawing processes (K. Goller, E. A. Galinski, Journal of Molecular Catalysis B: Enzymatic 7 (1999) pp37–45).

LDH reaction system is shown as follows:

L-lactic acid+NAD⁺ ⇌ Pyruvic acid+NADH+H⁺

A commercial LDH (5,000 U/ml) (Oriental Yeast Co., Ltd., from pig heart) was diluted with a 50 mM potassium phosphate buffer solution to prepare an about 250-unit enzyme solution. The enzyme solution thus prepared was dialyzed at 4° C. overnight to completely remove ammonium sulfate and the like contained in the commercial enzyme solution.

The dialyzed enzyme solution was diluted with a 50 mM potassium phosphate buffer solution to prepare an about 4-unit LDH solution.

A potassium phosphate buffer solution and the LDH solution were mixed and the resulting mixture was preincubated at 25° C., after which sodium pyruvate and NADH were quickly added and change in absorbance at 340 nm was measured for 5 minutes using a spectrophotometer (Beckman, DU640).

Composition of a reaction solution for LDH activity measurement and measuring conditions for the spectrophotometer are shown below.

[Composition of reaction solution]

| | |
|---|---|
| 0.1 M Potassium phosphate buffer (pH 7.0) | 3.00 ml |
| 25.4 mM Sodium pyruvate | 0.10 ml |
| NADH [10 mg/ml (10 mM Tris)] | 0.05 ml |
| Lactate dehydrogenase (LDH from pig heart, 4 U/ml) | 0.02 ml |
| | 3.17 ml |

[Measuring Conditions]
Wavelength: 340 nm
Optical path length: 1 cm
Temperature: 25° C.

LDH activity was determined from change in NADH (change in absorbance at 340 nm) using the following formula (i)

$$(\Delta A/\text{min} \cdot V \cdot D)/(\epsilon \cdot d \cdot v) = \text{IU/ml} \quad (i)$$

wherein $\Delta A/\text{min}$ = change in absorbance at 340 nm per minute,

V = final liquid volume (3.17 ml),

D = final dilution rate, $\epsilon$ = molecular absorption coefficient of NADH at 340 nm ($6.3 \times 10^3$ l·mole⁻¹·cm⁻¹), d = optical path length (1 cm), and v = volume of enzyme solution (0.02 ml).

The purified SP was added at concentrations of 0.01% and 0.05% to the LDH solutions (about 4 unit/ml) prepared by the abovementioned method.

To prepare control LDH solutions for comparison, bovine serum albumin (BSA) (Sigma, Albumin bovine fraction V) that is used as an agent for preventing freeze-induced decrease in protein activity was added at a concentration of 0% (potassium phosphate buffer only), 0.01%, and 0.1% to the LDH solutions.

The sample LDH solutions thus prepared are summarized as follows:

LDH [4 unit/ml],

LDH [4 unit/ml]+0.01% SP

LDH [4 unit/ml]+0.05% SP

LDH [4 unit/ml]+0.01% BSA

LDH [4 unit/ml]+0.05% BSA

Next, a 100 μl portion of each of the prepared samples was dispensed into a 1.5-ml test tube and frozen for 1 minute with liquid nitrogen. Then, after thawing at 30° C. for 5 minutes, LDH activity was measured by the abovementioned method. Remaining LDH activity for each sample after repeating freezing/thawing cycles was expressed by setting the LDH activity before freezing to 100%.

The remaining LDH activity in the samples without SP was markedly decreased by repetitive freezing/thawing cycles and was about 3% after 8 freezing/thawing cycles, while the sample with SP had about 90% remaining activity.

Figure 3:
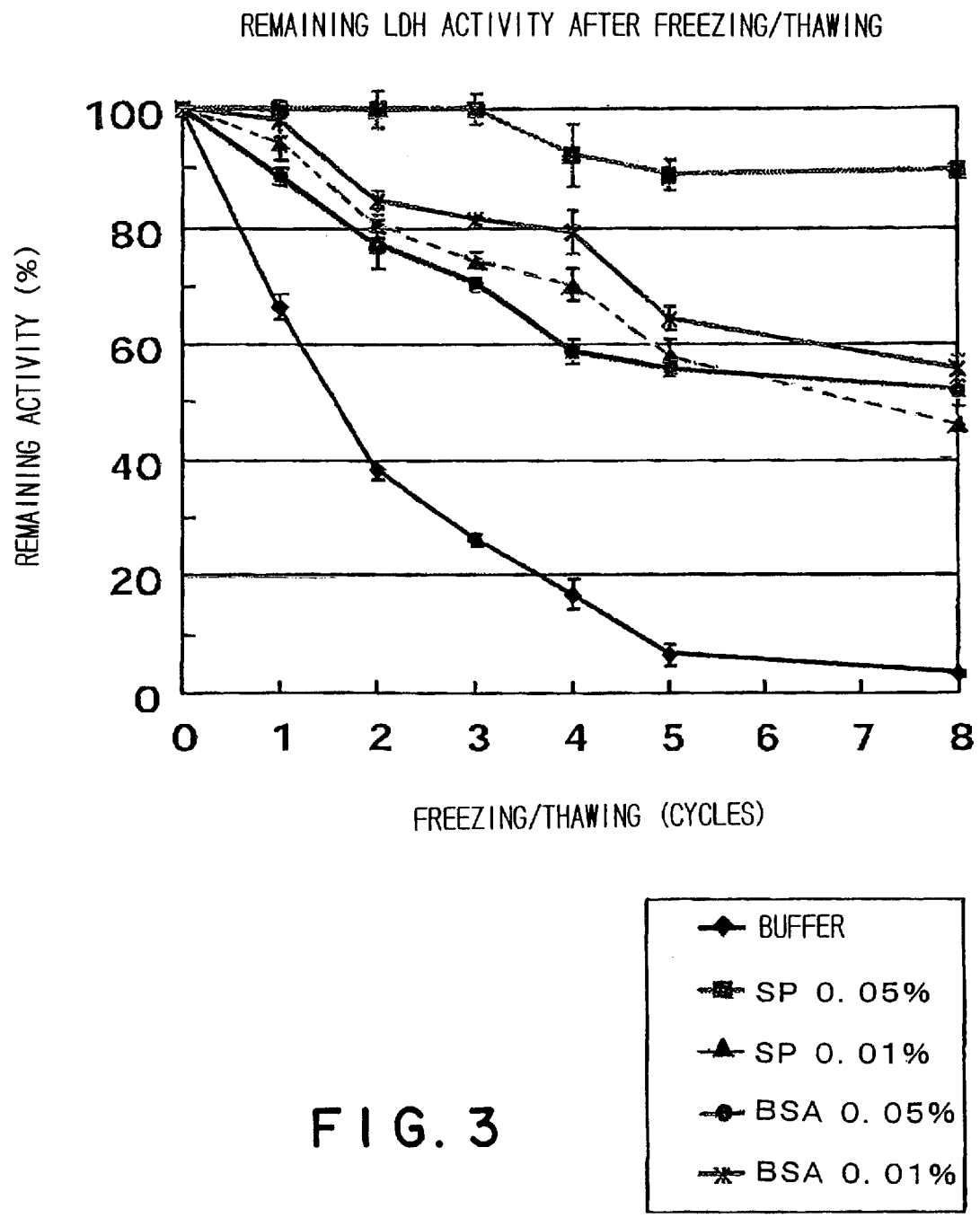
FIG. 3 shows the result of a test to evaluate activity of SP in protecting enzyme against freezing stress.

The abovementioned results are shown in FIG. 3.

What is claimed is:

1. A method for preventing freeze-induced decrease in activity of a protien of interest comprising adding a polypeptide comprising the following amino acid sequence (I) to the protein of interest: Ser-Sesr-Thr-Gly-Ser-X1-Ser-X2-Thr-Asp-X3-X4-X5-X6-X7-X8-Gly Ser-X9-Thr-Ser-Gly-Gly-Ser-Ser-Thr-Tyr-Gly-Tyr-Ser-Ser-X10-X11-X12-X13-Gly-X14-Val (I) (SEQ ID NO: 1) wherein, X1 represents Ser or Thr,
X2 represents Asn or Thr,
X3 represents Aer or Ala,
X4 represents Asn or Ser,
X5 represents Ser or Thr,
X6 represents Asn, Asp, or Lys,
X7 represents Ser, Asn, or Lys,
X8 represents Ala, Thr, or Val,
X9 represents Ser, or Arg,
X10 represents Asn, Ser, Asp, or Arg,
X11 represents Ser, Asn, His, or Cys,
X12 represents Arg or Gly,
X13 represents Asp or Gly, and
X14 represents Ser or Arg.

2. The method according to claim 1, wherein said amino acid sequence (I) is the following amino acid sequence (II):

Ser-Ser-Thr-Gly-Ser-Ser-Ser-Asn-Thr-Asp-Ser-Asn-Ser-Asn-Ser-Ala-Gly-Ser-Ser-Thr-Ser-Gly-Gly-Ser-Ser-Thr-Tyr-Gly-Tyr-Ser-Ser-Asn-Ser-Arg-Ala-Gly-Ser-Ser-Thr-Ser-Gly-Gly-Ser-Ser-Thr-Tyr-Gly-Tyr-Ser-Ser-Asn-Ser-Arg-Asp-Gly-Ser-Val-(II) (SEQ ID NO: 2).

3. The method according to claim 1, wherein said polypeptide comprises a repetitive sequence in which said amino acid sequence (I) is repeated at least twice.

4. The method according to claim 1, wherein said polypeptide is a chimeric protein.

5. The method according to claim 1, wherein said polypeptide is obtained by a method comprising:

providing a recombinant vector comprising a DNA encoding a polypeptide comprising the amino acid sequence (I), transforming a cell with said recombinant vector to obtain a transformant, and culturing said transformant and recovering a polypeptide from the resulting cells and/or culture thereof.

6. The method according to claim 1, wherein the protein of interest is an enzyme.

7. The method according to claim 2, wherein said polypeptide comprises a repetitive sequence in which said amino acid sequence (I) is repeated at least twice.

8. The method according to claim 2, wherein said polypeptide is a chimeric protein.

9. The method according to claim 3, wherein said polypeptide is a chimeric protein.

10. The method according to claim 7, wherein said polypeptide is a chimeric protein.

11. The method according to claim 2, wherein the protein of interest is an enzyme.

12. The method according to claim 3, wherein the protein of interest is an enzyme.

13. The method according to claim 4, wherein the protein of interest is an enzyme.

14. The method according to claim 5, wherein the protein of interest is an enzyme.

15. The method according to claim 7, wherein the protein of interest is an enzyme.

16. The method according to claim 8, wherein the protein of interest is an enzyme.

17. The method according to claim 9, wherein the protein of interest is an enzyme.

18. The method according to claim 10, wherein the protein of interest is an enzyme.

* * * * *

UNITED STATES PATENT AND TRADEMARK OFFICE
CERTIFICATE OF CORRECTION

PATENT NO.    : 6,887,979 B2                                             Page 1 of 1
DATED         : May 3, 2005
INVENTOR(S)   : Shigeru Nakamori et al.

It is certified that error appears in the above-identified patent and that said Letters Patent is hereby corrected as shown below:

<u>Title page,</u>
Item [56], insert -- Foreign Patent Documents 1302544
4/2003 European Pat. Off. --.

Signed and Sealed this

Twelfth Day of July, 2005

JON W. DUDAS
*Director of the United States Patent and Trademark Office*